United States Patent
Haider et al.

(10) Patent No.: US 9,233,221 B2
(45) Date of Patent: Jan. 12, 2016

(54) BITE BLOCK

(71) Applicant: Haider Biologics LLC, San Diego, CA (US)

(72) Inventors: Thomas T. Haider, Racho Santa Fe, CA (US); Gustavo R. Prado, San Diego, CA (US)

(73) Assignee: HAIDER BIOLOGICS LLC, San Diego, CA (US)

( * ) Notice: Subject to any disclaimer, the term of this patent is extended or adjusted under 35 U.S.C. 154(b) by 0 days.

(21) Appl. No.: 14/275,672

(22) Filed: May 12, 2014

(65) Prior Publication Data

US 2014/0332009 A1    Nov. 13, 2014

Related U.S. Application Data

(60) Provisional application No. 61/822,801, filed on May 13, 2013, provisional application No. 61/837,074, filed on Jun. 19, 2013, provisional application No. 61/846,993, filed on Jul. 16, 2013.

(51) Int. Cl.
*A61M 16/00* (2006.01)
*A61M 16/04* (2006.01)
*A61M 16/06* (2006.01)

(52) U.S. Cl.
CPC ....... *A61M 16/0493* (2014.02); *A61M 16/0497* (2013.01); *A61M 16/0688* (2014.02)

(58) Field of Classification Search
CPC ..................... A61M 16/0493; A61M 16/0463; A61M 16/0497; A61M 16/0488
USPC ........... 128/200.26, 207.14–207.17, 859–862
See application file for complete search history.

(56) References Cited

U.S. PATENT DOCUMENTS

| | | | |
|---|---|---|---|
| 2,908,269 A * | 10/1959 | Cheng | 600/237 |
| 4,261,354 A | 4/1981 | Nelson | |
| 4,275,725 A | 6/1981 | Nelson | |
| 4,289,127 A | 9/1981 | Nelson | |
| 4,326,515 A * | 4/1982 | Shaffer et al. | 128/207.17 |
| 4,329,984 A | 5/1982 | Kervin | |
| 4,425,911 A | 1/1984 | Luomanen et al. | |
| 4,495,945 A | 1/1985 | Liegner | |
| 5,626,128 A * | 5/1997 | Bradley et al. | 128/200.26 |
| 5,806,516 A * | 9/1998 | Beattie | A61M 16/0488 128/207.14 |
| 5,941,246 A | 8/1999 | Roopchand | |
| 6,098,627 A * | 8/2000 | Kellner et al. | 128/859 |
| 6,318,371 B1 * | 11/2001 | Tyszkiewicz | 128/859 |
| 8,001,964 B2 | 8/2011 | McDonald et al. | |
| 8,656,925 B2 * | 2/2014 | Davis et al. | 128/861 |
| 2007/0006878 A1 * | 1/2007 | Mackey et al. | 128/200.26 |
| 2007/0135770 A1 * | 6/2007 | Hunt | A61B 1/00154 604/174 |
| 2008/0257358 A1 * | 10/2008 | Stern | A61F 5/566 128/207.16 |

(Continued)

OTHER PUBLICATIONS

EcoSmedic: Endotracheal Tube Protector with Security Ring, first captured Jan. 22, 2009.

(Continued)

*Primary Examiner* — Justine Yu
*Assistant Examiner* — Kathrynn Reilly
(74) *Attorney, Agent, or Firm* — Wilson Sonsini Goodrich & Rosati

(57) ABSTRACT

A bite block and methods of use thereof are disclosed. The bite block may be configured to encompass a tube such as an endotracheal tube, and to protect the mouth of an intubated patient from clenching damage.

15 Claims, 9 Drawing Sheets

(56) References Cited

U.S. PATENT DOCUMENTS

2010/0180900 A1* 7/2010 Talsma et al. ............ 128/207.14
2011/0132380 A1* 6/2011 Goldsby ....................... 128/861

OTHER PUBLICATIONS

EcoSmedic: Bite Block first captured Jan. 22, 2009.
B&B Medical Technologies: Universal Bite Block (Adult), Prevents ET tube occlusion while biting; protects against pilot balloon rupture, located at http://bandb-medical.com/universal-bite-block-adult/, May 2008.
Respiratory Therapy (2008) April-May, 3(2):2. Advertisement for B&B Medical Technologies: Universal Bite Block.

US Endoscopy: Bite Blocks, available Aug. 24, 2010 at http://www.usendoscopy.com/endoscopy/endoscope-care-and-accessories/bite-blocks.aspx.

* cited by examiner

BITE BLOCK

CROSS-REFERENCE

This application claims the benefit of U.S. Provisional Application No. 61/822,801, filed May 13, 2013, 61/837,074, filed Jun. 19, 2013, and 61/846,993, filed Jul. 16, 2013, each of which is hereby explicitly incorporated herein by reference in its entirety.

SUMMARY OF THE INVENTION

Provided herein are embodiments related to a bite block to be used by a health care provider and more particular to a bite block that will be secured to an endotracheal tube or similar device.

Current bite blocks and mouth guards used in intubated patients do not provide anchoring for the endotracheal tube while protecting the teeth and soft tissues of the mouth. Injuries of the soft tissues of the mouth are common in procedures where intubation occurs, especially if the procedure requires patient repositioning such as in orthopedic surgeries. In addition, endotracheal tube migration can be life-threatening if it goes unnoticed.

The current disclosure relates to devices and methods comprising a clamp and a body, such as Surgical Bite Block, and use thereof, for example to hold in place a device such as an endotracheal tube. The tube clamp is generally made from a flexible material such as Nylon or Acetal plastic with or without fiber glass reinforcement or other reinforcement such as medical grade plastic. The tube clamp generally clamps around an endotracheal tube such that the invention is affixed to the endotracheal tube. The tube clamp is generally positioned outside the mouth of the patient when properly deployed, although embodiments wherein the tube clamp is positioned within the mouth of a patient when the device is deployed are also contemplated. The body is generally made from a soft material, such as Silicone or a medical grade foam. In some embodiments, when properly deployed, the body preferentially rests inside the mouth of the patient thereby anchoring the invention inside the patient's mouth. The bite block anchors the endotracheal tube inside the patient, prevents it from migrating and protects the mouth and teeth of the patient.

Some embodiments relate to a bite block comprising: a body comprising an outer surface and a first portion sized and shaped to fit in the mouth of a person; an endotracheal tube clamp sized to fit accommodate an endotracheal tube therein and coupled to the body; a first channel running through the body sized to fit accommodate the endotracheal tube therein; and a slit extending from the outer surface of the body and joining the first channel that allows the endotracheal tube to be placed in the first channel or removed from the first channel. In some aspects the first channel is round or ovoid. In some aspects, the body comprises an outer surface. In some aspects, the bite block further comprises a slit extending from the outer surface of the body and joining the first channel. In some aspects, the slit allows an endotracheal tube to be placed in the first channel. In some aspects, the slit allows an endotracheal tube to be removed from the first channel. In some aspects, the slit is bounded by rounded edges on the outer surface of the body. In some aspects, the rounded edges protect the lips of a patient from pinching damage when the body is applied to the patient's mouth. In some aspects, the body further comprises a second channel running through the body. In some aspects, the second channel joins the slit. In some aspects, the second channel is round or ovoid. In some aspects, a first arm that connects the body is coupled to the endotracheal tube clamp by a first arm. In some aspects, the first arm is at least one of: molded into the body, attached to the body with screws, and attached to the body with adhesive. In some aspects, the first arm is made out of a flexible material. In some aspects, the flexible material is a medical grade plastic. In some aspects, the medical grade plastic is at least one of Acetal, and Nylon plastic. In some aspects, the medical grade plastic is Nylon plastic. In some aspects, the medical grade plastic is supplemented with 20%-40% fiberglass. In some aspects, the medical grade plastic is supplemented with 30% fiberglass. In some aspects, the body is coupled to the endotracheal tube clamp by a second arm. In some aspects, the second arm is at least one of: molded into the body, attached to the body with screws, and attached to the body with adhesive. In some aspects, the bite block comprises a neck strap connection. In some aspects, the neck strap connection is attached to an arm. In some aspects, the neck strap connection is molded into an arm. In some aspects, the neck strap connection is attached to the endotracheal tube clamp. In some aspects, the neck strap connection is attached to the body. In some aspects, the neck strap connection is at least one of a ring, a hollow rectangle, a slit or a post. In some aspects, the bite block further comprises a finger support. In some aspects, the finger support is a part of the first arm. In some aspects, a neck strap connection is a part of the finger support. In some aspects, the finger support is attached to the first arm. In some aspects, the finger support is either a ring or a hollow rectangle. In some aspects, the body is at least one of spherical, cylindrical or ovoid shape. In some aspects, the body is made of a soft material. In some aspects, the soft material is Silicone. In some aspects, the soft material is a medical grade foam. In some aspects, the endotracheal tube clamp comprises a locking mechanism. In some aspects, the locking mechanism has a single locking position. In some aspects, the locking mechanism has multiple locking positions. In some aspects, the locking mechanism comprises a latch. In some aspects, the latch comprises at least one of and a hook and a notch, a hook and a plurality of notches, or a pair of hooks. In some aspects, the locking mechanism comprises at least one of a pair of magnets, a zip tie, a reversible zip tie, and a nut and bolt. In some aspects, the locking mechanism comprises a pair of handles for opening and closing the locking mechanism. In some aspects, the endotracheal tube clamp comprises a series of ridges on an interior of the clamp. In some aspects, the endotracheal tube is made of a flexible material. In some aspects, the flexible material is a medical grade plastic. In some aspects, the medical grade plastic is Acetal plastic. In some aspects, the body comprises a first groove for a patient's teeth or gums. In some aspects, the body comprises a second groove for the patient's teeth or gums opposite the first groove. In some aspects, the first groove extends around the circumference of the body. In some aspects, the first groove and the second groove extend into the first channel. In some aspects, the body comprises an anterior aspect and a posterior aspect. In some aspects, the posterior aspect is at least one of bulbous, cylindrical, and spherical. In some aspects, the anterior aspect is at least one of cylindrical spherical.

Some embodiments relate to a bite block comprising: a bipartite body comprising a first body piece and a second body piece separated by a slit and sized and shaped to fit in combination into a mouth of a patient, an endotracheal tube clamp, and a first channel running through the body. In some aspects, the first body piece and the second body piece are held together by the endotracheal tube clamp. In some aspects, the endotracheal tube clamp has a first locking mechanism and a second locking mechanism. In some aspects, at least one of the first locking mechanism and the second locking mechanism comprises a latch. In some aspects, the latch comprises at least one of and a hook and a notch, a hook and a plurality of notches, and a pair of hooks. In some aspects, at least one of the first locking mechanism and the second locking mechanism comprises at least one of a pair of magnets, a zip tie, a reversible zip tie, and a nut and bolt. In some aspects, the first channel is either round or ovoid. In some aspects, the body further comprises a second channel. In some aspects, the second channel intersects the first channel. In some aspects, the second channel is either round or ovoid. In some aspects, the body is made of a soft material. In some aspects, the soft material is Silicone. In some aspects, the soft material is a medical grade foam. In some aspects, at least one of the first locking mechanism the second locking mechanism comprises a pair of handles for opening and closing the locking mechanism. In some aspects, the endotracheal tube clamp comprises a series of ridges on an interior of the clamp. In some aspects, the endotracheal tube is made of a flexible material. In some aspects, the flexible material is a medical grade plastic. In some aspects, the medical grade plastic is Acetal plastic. In some aspects, the body comprises a first groove for a patient's teeth or gums. In some aspects, the body comprises a second groove for the patient's teeth or gums opposite the first groove. In some aspects, the first groove extends around the circumference of the body. In some aspects, the first groove and the second groove extend into the first channel. In some aspects, the body comprises an anterior aspect and a posterior aspect. In some aspects, the posterior aspect is at least one of bulbous, cylindrical, and spherical. In some aspects, the anterior aspect is at least one of cylindrical spherical.

Some embodiments relate to a method of protecting a patient's mouth from clenching damage during endotracheal tube administration, comprising the steps of surrounding a segment of an endotracheal tube with a soft body held to the endotracheal tube by at least a clamp, and deploying the body to the interior of a patient's mouth. In some aspects, said clamp may be reversibly released from said endotracheal tube. In some aspects, said clamp may be configured to engage said endotracheal tube in a plurality of clamp positions. In some aspects, said endotracheal tube may be adjusted when released from said clamp. In some aspects, said endotracheal tube may be deployed to a patient prior to holding said soft body to the endotracheal tube. In some aspects, said clamp grasps said endotracheal tube via a plurality of grooves in an interior of said clamp. In some aspects, said body is held in place by a neck strap holding said body in place in said patient's mouth. In some aspects, said body comprises at least one groove to accommodate patient teeth or gums, and wherein said body is held in place by a fit of said patient teeth or gums into said groove or grooves.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
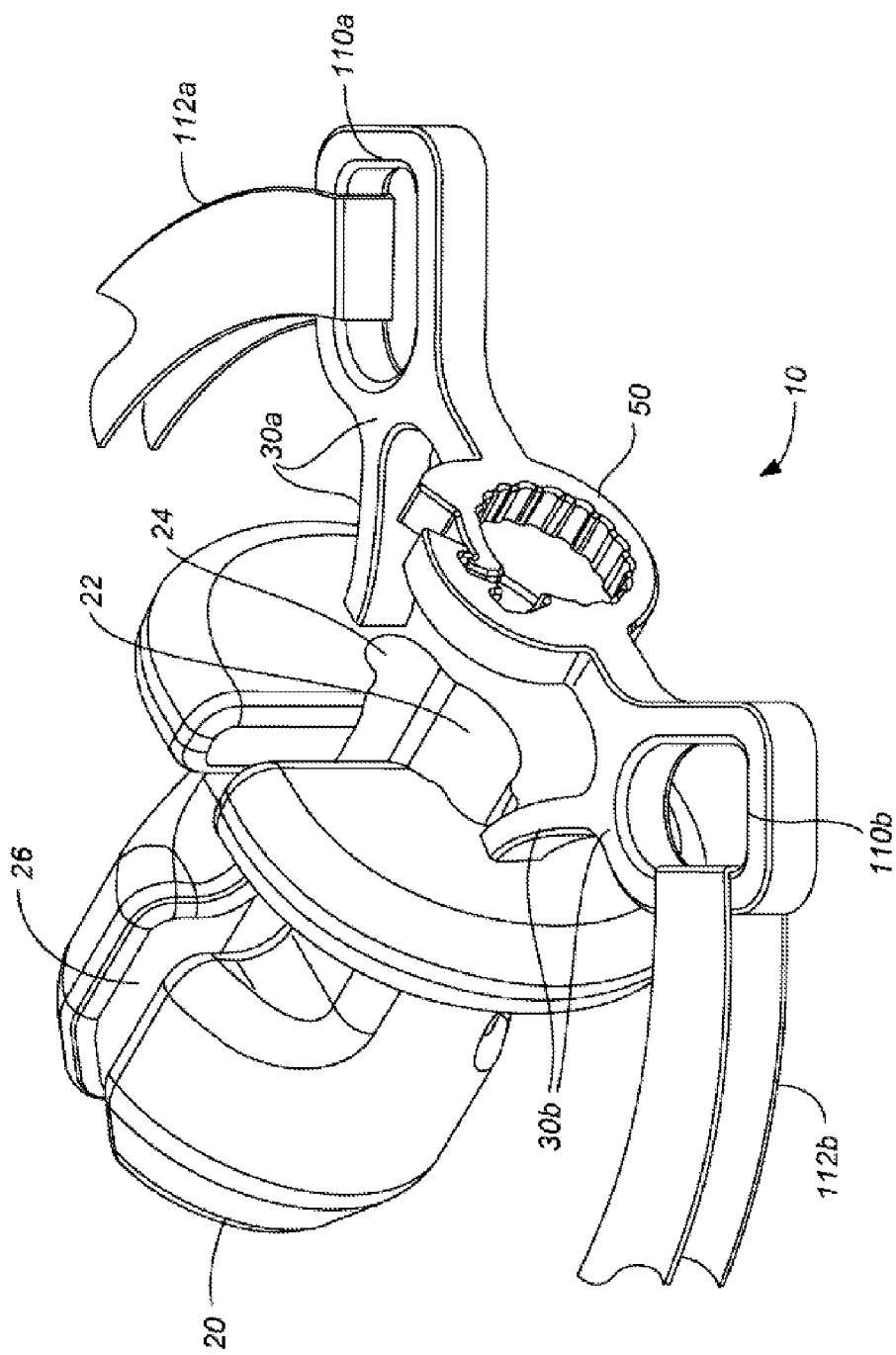
FIG. 1 shows an embodiment of the surgical bite block.

The disclosure herein comprises devices and methods related to a bite block comprising: a body comprising an outer surface and a first portion sized and shaped to fit in the mouth of a person; an endotracheal tube clamp sized to fit accommodate an endotracheal tube therein and coupled to the body; a first channel running through the body sized to fit accommodate the endotracheal tube therein; and a slit extending from the outer surface of the body and joining the first channel that allows the endotracheal tube to be placed in the first channel or removed from the first channel.

In some embodiments the disclosure herein concerns a bite block which comprises: a body sized and shaped to fit in a mouth of a person, wherein said body comprises a soft material such as Silicone, and wherein said body comprises: a) a first groove and a second groove into which teeth of said patient may fit to stabilize said body when said body is deployed into the mouth of said patient, b) a first channel running through the body sized to accommodate the endotracheal tube therein, c) a second channel sized to accommodate a measuring device, running parallel to said first channel within said body, and d) a slit extending from an outer surface of the body and joining the first channel said slit comprising rounded edges at said outer surface to protect the mouth of said person when said body is deployed into the mouth of said patient; and wherein said bite block further comprises an endotracheal tube clamp sized to accommodate an endotracheal tube therein and coupled to the body, e) wherein said endotracheal tube comprises a locking mechanism, said locking mechanism comprising a latch, said latch comprising a hook and at least one notch in an opposing configuration relative to said hook such that said hook and said notch may engage to hold said latch in a closed configuration, f) wherein said latch in said closed configuration is capable of holding an endotracheal tube passed there through substantially in place, and g) wherein said latch in a second open configuration does not comprise said hook engaged with said notch, and h)

wherein said latch in said open configuration is not capable of holding an endotracheal tube passed there through substantially in place, i) said endotracheal tube clamp further comprising openings through which a neck strap may be threaded to said endotracheal tube clamp and said body in place when said body is deployed into the mouth of a person.

Some embodiments relate to methods of protecting a patient's mouth from clenching damage during endotracheal tube administration, comprising the steps of surrounding a segment of an endotracheal tube with a soft body held to the endotracheal tube by at least a clamp, and deploying the body to the interior of a patient's mouth.

Embodiments may comprise one or more of the following elements.

Body. A bite block may comprise a body capable of being inserted into the mouth of a patient. A number of body shapes are consistent with the disclosure herein. In some embodiments the body is round, cylindrical, oval, lozenge-shaped, a cylindrical ellipse, a cylindrical hexagon, a cylindrical octagon, or other shape consistent with insertion into a patient's mouth. In some embodiments, the body is spherical. In some embodiments, the body is cylindrical. In some embodiments the body is ovoid. In some embodiments any shape consistent with this element is contemplated. Alternative body shapes consistent with the disclosure herein may share the element of capability of being inserted into the mouth cavity of a patient.

In some embodiments the body is bilaterally symmetrical along its long axis, or otherwise along the axis parallel with the long axis of a patient's throat cavity.

In some embodiments the body comprises a first channel running through its center. In some embodiments the first channel is sized and shaped to accommodate a tube, such as an endotracheal tube, to pass therethrough. In some embodiments the diameter of the first channel ranges from 2 to 15 mm, for example 2, 3, 4, 5, 6, 7, 8, 9, 10, 11, 12, 13, 14, or 15 mm, or any non-integer value within said range of 2 to 15 mm. In some embodiments the channel is accompanied by a second channel, such as a second channel in parallel or intersecting the first channel that is configured to accommodate a sensor such as a temperature probe. In some embodiments, the first channel is sized, shaped or sized and shaped to allow at least one other device such as at least one temperature probe to pass through the first channel. In some embodiments, the first channel is circular in cross section. In some embodiments, the first channel is elliptical in cross section. In some embodiments the first channel is triangular, rectangular, pentagonal, hexagonal, heptagonal, octagonal, or demonstrates alternative regular or irregular geometry in cross section. In some embodiments only an endotracheal tube may pass through the first channel.

In some embodiments the body is divided along or parallel to its long axis or otherwise along the channel discussed above. In some embodiments the body is divided so as to allow the body to be split apart and to be reconstituted around a tube, such as an endotracheal tube deployed to a patient. In some embodiments the tube such as an endotracheal tube is positioned to pass through a first channel of the body. In some embodiments the body is divided from one surface through to a first central channel, while in other embodiments the body is divided from one surface through to a second surface, so that it is partially or totally split into halves or unequal fractions. The edges of the body may be rounded or otherwise softened so that reconstitution of the body within the mouth of a patient does not pinch or crush patient mouth tissue.

In some embodiments the second channel is connected to the first channel. In some embodiments, the second channel intersects the first channel. In some embodiments the second channel allows at least one other device such as at least one temperature probe to pass through the body. In some embodiments, the bite block comprises a slit on the body. In some embodiments the slit is coplanar with the first channel. In some embodiments the slit is on the superior side of the body. In some embodiments, the slit is on the inferior side of the body. In some embodiments, the slit extends into the first channel. In some embodiments the slit allows an endotracheal tube or other devices to slide through the slit and into the first channel. In some embodiments, the slit intersects the second channel. In some embodiments, the slit extends completely through the first channel and divides the body into two pieces. In some embodiments the two pieces of the body are held together by the endotracheal tube clamp.

The body may be made of any soft, durable substances. In some embodiments the body is made of silicone. In some embodiments the body is made of a synthetic foam such as a medical grade foam.

In some embodiments, the body connects to the endotracheal tube clamp at a first arm or a first arm and a second arm. In some embodiments the body is molded around the first arm or the first and second arms. In some embodiments, the first arm or the first and second arms are attached to the body with one or more screws. In some embodiments, the first arm or the first and second arms are attached to the body with an adhesive. In some embodiments, the first arm or the first and second arms are made of a flexible material. In some embodiments the first arm or the first and second arms are made of a flexible material such as Acetal or Nylon plastic or other medical grade plastic. In some embodiments the Acetal or Nylon plastic or other medical grade plastic is reinforced with fiber glass reinforcement or other medical grade plastic. In some embodiments the reinforcement is present at 20, 21, 22, 23, 24, 25, 26, 27, 28, 29, 30, 31, 32, 33, 34, 35, 36, 37, 38, 39, or 40%, or any non-integer value within a range of 20% to 40%. In some embodiments the flexible material is Nylon, reinforced with 30% fiberglass. In some embodiments, the first arm or the first and second arms are shaped and positioned such that they allow concurrent opening of the endotracheal tube clamp and the body, for example to ease the placement of the endotracheal tube. In some embodiments the first arm or the first and second arms are curved. In some embodiments, the first arm or the first and second arms are S shaped.

In some embodiments, the device comprises a neck strap having ends and a neck strap connection. In some embodiments, the neck strap connection is attached to the first arm 30a or the first and second arms. In some embodiments, the neck strap connection is built into the first arm. A number of neck strap configurations are consistent with the disclosure herein. In some embodiments, the neck strap connections are each a ring. In some embodiments the neck strap connections are each rectangular. In some embodiments, the neck strap connections are each a clip. In some embodiments, the neck strap connections are each a post. In some embodiments, the neck strap having ends fits around the patient's neck to further secure the device to the patient.

In some embodiments the body comprises a groove on its top surface relative to a standing patient, its bottom surface, or its top and its bottom surface. In some embodiments the top groove accommodates a patient's teeth or gums when the body is deployed into a patient mouth. In some embodiments the bottom groove accommodates a patient's bottom teeth when the body is deployed into a patient mouth. In some embodiments, the top and or bottom groove may align with a patient's teeth or gums. In some embodiments the bite block comprises a body with a first groove. In some embodiments, the patient's teeth or gums rest within the first groove, further securing the body in the patient's mouth when the body is properly deployed into a patient's mouth. In some embodiments, the body has a second groove. In some embodiments, the patient's lower teeth or gums rest in the second groove and the patient's upper teeth and gums rest in the first groove when the body is properly deployed into a patient's mouth. In some embodiments, the first groove extends circumferentially around the body. In some embodiments, either the first or second groove or both comprise a concave indent on the body. In some embodiments, the slit intersects the first groove or the second groove or both the first groove and the second groove. In some embodiments, the slit has an anti-pinch feature that protects the patient's lips. In some embodiments the first groove or the second groove or the first groove and the second groove have an anti-pinch feature, such as an anti-pinch feature that protects the patient's lips. The anti-pinch feature may comprise a rounded edge or edges at regions likely to contact a patient's lips when the device is properly deployed. In some embodiments, the body comprises a second set of concave indents to support the patient's lips. Some embodiments lack one or more of the first groove and the second groove.

In some embodiments, the body's shape promotes the anchoring of the bite block in the patient's mouth when the body is properly deployed. In some embodiments this occurs due to a natural tendency of the patient's mouth to rest in a semi-closed position. The patient's teeth or gums then rest on the groove(s) thereby anchoring the construct in the patient's mouth. In some embodiments, the body has an anterior aspect and a posterior aspect. In some embodiments, the body's posterior aspect has a bulbous shape that passively anchors in the mouth by resting proximal to the front teeth or front gums. The body keeps the patient's mouth open enough to clear the endotracheal tube while minimizing stresses on both the patient's soft tissues and teeth. This embodiment comprises a first groove and a second groove that provide space for the teeth or gums to rest on and further stabilizing the bite block 10 in the anterior-posterior axis. Some embodiments of the body lack a first or a second groove. Accordingly, in some embodiments patient's teeth rest directly on the body or anterior to the body when the body is properly deployed in a patient's mouth.

In some embodiments the body is attached to a tube clamp. In some embodiments the body is reversibly attached to a tube clamp. In some embodiments the body may be removed from a tube clamp. In some embodiments the body is detachable from a tube clamp. In some embodiments the body is irreversibly attached to a tube clamp. In some embodiments the body is fabricated in connection with a tube clamp.

Tube clamp. In some embodiments a body is connected to a tube clamp, such as an endotracheal tube clamp. In some embodiments an endotracheal tube clamp may clasp an enclosed tube such as an endotracheal tube, holding the attached body in position relative to the endotracheal tube. In some embodiments the size of inner diameter of the tube clamp is tailored to accommodate therein an endotracheal tube such as that depicted in element 100 of FIG. 3, below wherein the endotracheal tube has an inner diameter of 2.5 to 8.5 mm, for example, 2.5, 3.0, 3.5, 4.0, 4.5, 5.0, 5.5, 6.0, 6.5, 7.0, 7.5, 8.0, or 8.5 mm, or any non-integer value within said range of 2.5 to 8.5 mm, at various levels of material interference. In some embodiments the tube clamp interior comprises a plurality of ridges that further clasp a tube such as an endotracheal tube clamped therein.

In some embodiments the tube clamp comprises a latch. Some latch embodiments comprise at least one hook and at least one notch, such that a hook and a notch may engage to restrict the inner diameter of the tube clamp. In some embodiments a plurality of notches are provided, thereby allowing for a plurality of tube clamp inner diameters upon engagement of a notch and a latch. In some embodiments a tube clamp is secured by a magnet, a plurality of magnets, or a zip clip such as a reversibly closable zip clip.

In some embodiments tube clamp components such as a notch and a latch comprise one or more tabs or protrusions or handles through which the notch or latch or both notch and latch are manipulated. In some embodiments such manipulation comprises displacing one or both of the latch and notch laterally with respect to its counterpart such that the latch and notch cease to be engaged. In some embodiments, the endotracheal tube clamp comprises a locking mechanism. In some embodiments, the endotracheal tube clamp has multiple locking mechanisms. In some embodiments, the locking mechanism has a single locking position. In some embodiments, the locking mechanism has multiple locking positions. In some embodiments, the locking mechanism comprises a latch system. In some embodiments, the latch system comprises a hook and a notch that fit together. In some embodiments the latch system comprises a hook with a plurality of notches. In some embodiments the latch system comprises a plurality of hooks. In some embodiments each notch defines a distinct locking position when interfaced with a hook.

In some embodiments, the locking mechanism comprises a handle, or a pair of handles for engaging and disengaging the locking mechanism. In some embodiments, the locking mechanism comprises a pair of handles for engaging and disengaging the locking mechanism. In some embodiments the handles correspond to the neck strap connections.

In some embodiments, the locking mechanism comprises a nut and bolt. In some embodiments, the locking mechanism comprises a magnet, a pair of magnets, or a larger plurality of magnets. In some embodiments, the locking mechanism comprises a zip tie. In some embodiments, the locking mechanism comprises a reversible zip tie. In some embodiments, an interior surface of the endotracheal tube clamp comprises from one to a series of ridges. In some embodiments the series of ridges can grip an enclosed device such as an endotracheal tube when the endotracheal tube clamp is in the locked position. In some embodiments, the endotracheal tube clamp is made of a flexible material such as Acetal or Nylon plastic or other medical grade plastic. In some embodiments the Acetal or Nylon plastic or other medical grade plastic is reinforced with fiber glass reinforcement or other medical grade plastic. In some embodiments the reinforcement is present at 20, 21, 22, 23, 24, 25, 26, 27, 28, 29, 30, 31, 32, 33, 34, 35, 36, 37, 38, 39, or 40%, or any non-integer value within a range of 20% to 40%. In some embodiments the flexible material is Nylon, reinforced with 30% fiberglass.

In some embodiments, the tube clamp is attached to at least one neck strap connection. Neck strap connections comprising loops, rectangular openings, slits, or studs are all consistent with embodiments disclosed herein. In some embodiments the neck strap connections comprise loops. In some embodiments the neck strap connections comprise rectangular openings. In some embodiments the neck strap connections comprise slits. In some embodiments the neck strap connections comprise studs. A neck strap may be deployed to interface with the at least one neck strap connection, such as a pair of neck strap connections on alternate sides of the tube clamp, so as to hold the tube clamp, body and any enclosed tube in place when properly deployed to a patient. In some embodiments the neck strap connections serve as handles that are used to manipulate the tube clamp.

The tube clamp, handles and neck strap connections (or neck strap connection/handles, if the elements are convergent) may be formed of any solid substance. In some embodiments the above-mentioned components are made of medical grade plastic such as Acetal or Nylon plastic. In some embodiments the medical grade plastic such as Acetal or Nylon plastic is reinforced with fiber glass, such as 20, 21, 22, 23, 24, 25, 26, 27, 28, 29, 30, 31, 32, 33, 34, 35, 36, 37, 38, 39, or 40%, or any non-integer value within a range of 20% to 40%. In some embodiments the flexible material is Nylon, reinforced with 30% fiberglass.

In some embodiments the tube clamp is attached to a body. In some embodiments the tube clamp is reversibly attached to a body. In some embodiments the tube clamp may be removed from a body. In some embodiments the tube clamp is detachable from a body. In some embodiments the tube clamp is irreversibly attached to a body. In some embodiments the tube clamp is fabricated in connection with a body.

In some embodiments, the bite block may comprise finger supports that allow the healthcare provider to open and close the endotracheal tube clamp. In some embodiments, the finger supports are located between the first or second arm and the endotracheal tube clamp. In some embodiments the finger supports are a ring or a pair of rings. In some embodiments the finger supports are rectangular. In some embodiments, pushing the finger supports towards each other locks the endotracheal tube clamp. In some embodiments, the neck strap connection comprises holes or slits located on the finger supports. In some embodiments, the finger supports are rectangular with an opening in the middle. In some embodiments, the neck strap connection is the opening in the finger supports. In some embodiments, the finger supports allow easy locking and unlocking of the endotracheal tube clamp.

Some embodiments relate to methods of protecting a patient's mouth or teeth or mouth and teeth from clenching damage during intubation. Some embodiments relate to methods of fixing a tube such as an endotracheal tube in place while protecting a patient's mouth or teeth or mouth and teeth from clenching damage during intubation. Some embodiments comprise positioning a body into a patient's mouth. Some embodiments comprise fixing the body to a tube, such as an endotracheal tube, through a tube clamp. In some embodiments the body is held in place through a neck strap connected to the body, for example through neck strap connections. In some embodiments the body is held in place through a patient's own teeth or gums, which clamp down on the body. In some embodiments a patient's own teeth and gums clamp down on a body through a groove or grooves which assist the patient's own teeth and gums to hold the body in place. In some embodiments the body is positioned within a patient's mouth by a medical professional. In some embodiments the body is positioned to surround a cross section of a tube such as an endotracheal tube deployed into a patient. In some embodiments a tube clasp holds a tube such as an endotracheal tube in position within the mouth of a patient.

In one method of placement of the bite block, after the patient is intubated, a user such as a healthcare provider may open the endotracheal tube clamp by grasping the arms and applying a bending moment, for example causing the latch disengage as a result of the notch to move laterally along the long axis of the device relative to the hook, to open the endotracheal tube clamp until the endotracheal tube can pass through the locking mechanism. Alternately, a user such as a healthcare provider may open the endotracheal tube clamp by grasping the arms and applying a compressing motion to the arms, for example causing the latch to disengage as a result of the notch passing over and along the hook perpendicular to the long axis of the device. Other release methods are contemplated. By opening the endotracheal tube clamp, the slit may also open to allow the endotracheal tube to reach the first channel in the body. In some embodiments, the body opens because the endotracheal tube clamp is anchored into the lateral aspects of the body, and the first and second arms transfer the bending deflection to the body. Once the endotracheal tube clamp and the body are placed around an endotracheal tube such as the endotracheal tube the bite block may be allowed to translate along the longitudinal axis of the endotracheal tube in the unlocked position. The user such as a healthcare provider may then slide the bite block and introduce the body into the patient's mouth in a position that provides the protection of the patient's teeth and soft tissues. Once the desired position is found, the user such as a healthcare provider locks the clamp to secure the position of the bite block relative to the endotracheal tube. A neck strap then is attached to the neck strap connection to further stabilize the construct by securing the surgical bite block around the patient's neck. In some embodiments, body dimensions such as round body dimensions allow for the surgical bite block to swivel around the mouth in a ball and socket fashion to adjust endotracheal tube position, for example to compensate for an endotracheal tube that may not be placed centered with respect to the mouth openings of the patient.

Some embodiments relate to devices for use in protecting a patient's mouth or teeth or mouth and teeth from clenching damage during intubation. Some embodiments relate to devices for use in fixing a tube such as an endotracheal tube in place while protecting a patient's mouth or teeth or mouth and teeth from clenching damage during intubation. Some embodiments comprise positioning a body into a patient's mouth. Some embodiments comprise fixing the body to a tube, such as an endotracheal tube, through a tube clamp. In some embodiments the body is held in place through a neck strap connected to the body, for example through neck strap connections. In some embodiments the body is held in place through a patient's own teeth or gums, which clamp down on the body. In some embodiments a patient's own teeth and gums clamp down on a body through a groove or grooves which assist the patient's own teeth and gums to hold the body in place. In some embodiments the body is positioned within a patient's mouth by a medical professional. In some embodiments the body is positioned to surround a cross section of a tube such as an endotracheal tube deployed into a patient. In some embodiments a tube clasp holds a tube such as an endotracheal tube in position within the mouth of a patient.

In one deployment of a device for use to protect a patient's mouth or teeth or mouth and teeth from clenching damage during intubation, after the patient is intubated, a user such as a healthcare provider may open the endotracheal tube clamp by grasping the arms and applying a bending moment, for example causing the latch to disengage as a result of the notch moving laterally along the long axis of the device relative to the hook, to open the endotracheal tube clamp until the endotracheal tube can pass through the locking mechanism. Alternately, a user such as a healthcare provider opens the endotracheal tube clamp by grasping the arms and applying a compressing motion to the arms, for example causing the latch to disengage as a result of the notch passing over and along the hook perpendicular to the long axis of the device. Other release methods are contemplated. By opening the endotracheal tube clamp, the slit may also open to allow the endotracheal tube to reach the first channel in the body. In some embodiments, the body opens because the endotracheal tube clamp is anchored into the lateral aspects of the body, and the first and second arms transfer the bending deflection to the body. Once the endotracheal tube clamp and the body are placed around an endotracheal tube such as the endotracheal tube the bite block may be allowed to translate along the longitudinal axis of the endotracheal tube in the unlocked position. The user such as a healthcare provider then slides the bite block and introduce the body into the patient's mouth in a position that provides the protection of the patient's teeth and soft tissues. Once the desired position is found, the user such as a healthcare provider locks the clamp to secure the position of the bite block relative to the endotracheal tube. A neck strap may then be attached to the neck strap connection to further stabilize the construct by securing the surgical bite block around the patient's neck. In some embodiments, body dimensions such as round body dimensions allow for the surgical bite block to swivel around the mouth in a ball and socket fashion to adjust endotracheal tube position, for example to compensate for an endotracheal tube that may not be placed centered with respect to the mouth openings of the patient.

FIG. 1 shows an exemplary embodiment of a bite block 10. A bite block 10 may comprise a body 20 and an endotracheal tube clamp 50. The body 20 may comprise any shape that will fit within a patient's mouth. In some embodiments, the body 20 is spherical. In some embodiments, the body 20 is cylindrical. In some embodiments the body 20 is ovoid. Alternative body shapes consistent with the disclosure herein may share the element of capability of being inserted into the mouth cavity of a patient. In some embodiments any shape consistent with this element is contemplated. In some embodiments, the body 20 is made of a soft material. In some embodiments, the body 20 is made of a soft material such as Silicone or a medical grade foam. In some embodiments, the body 20 comprises a first channel 22 running through the body 20. In some embodiments, the first channel 22 is sized and shaped to allow a tube (such as an endotracheal tube as depicted in element 100 of FIG. 3, below) to pass through the first channel 22. In some embodiments the diameter of the first channel 22 ranges from 2 to 15 mm, for example 2, 3, 4, 5, 6, 7, 8, 9, 10, 11, 12, 13, 14, or 15 mm, or any non-integer value within said range of 2 to 15 mm. In some embodiments the size of the first channel 22 is tailored to accommodate therein an endotracheal tube such as that depicted in element 100 of FIG. 3, below wherein the endotracheal tube has an inner diameter of 2.5 to 8.5 mm, for example, 2.5, 3.0, 3.5, 4.0, 4.5, 5.0, 5.5, 6.0, 6.5, 7.0, 7.5, 8.0, or 8.5 mm, or any non-integer value within said range of 2.5 to 8.5 mm, at various levels of material interference. In some embodiments, the first channel 22 is sized, shaped or sized and shaped to allow at least one other device such as at least one temperature probe to pass through the first channel 22. In some embodiments, the first channel 22 is circular in cross section. In some embodiments, the first channel 22 is elliptical in cross section. In some embodiments the first channel is triangular, rectangular, pentagonal, hexagonal, heptagonal, octagonal, or demonstrates alternative regular or irregular geometry in cross section. In some embodiments, only an endotracheal tube such as that seen as element 100 of FIG. 3 can pass through the first channel 22. In some embodiments, other instruments can be placed through the first channel 22 alongside the endotracheal tube 100. In some embodiments, the body 20 comprises at least a second channel 24 or a plurality of channels. In some embodiments the second channel 24 is connected to the first channel 22. In some embodiments, the second channel 24 intersects the first channel 22. In some embodiments the second channel 24 allows at least one other device such as at least one temperature probe to pass through the body 20. In some embodiments, the bite block 10 comprises a slit 26 on the body 20. In some embodiments the slit 26 is coplanar with the first channel 22. In some embodiments the slit 26 is on the superior side of the body 20. In some embodiments, the slit 26 is on the inferior side of the body 20. In some embodiments, the slit 26 extends into the first channel 22. In some embodiments the slit allows an endotracheal tube such as the endotracheal tube 100 of FIG. 3, below, or other devices to slide through the slit 26 and into the first channel 22. In some embodiments, the slit 26, intersects the second channel 24. In some embodiments, the slit 26 extends completely through the first channel 22 and divides the body into two pieces. In some embodiments the two pieces of the body 20 are held together by the endotracheal tube clamp 50. A view of an embodiment of an endotracheal tube clamp 50 separate from a body is provided in FIG. 7, further discussed below. In some embodiments, the body 20 connects to the endotracheal tube clamp 50 at a first arm 30a or a first arm 30a and a second arm 30b. In some embodiments the body 20 is molded around the first arm 30a or the first and second arms 30a and 30b. In some embodiments, the first arm 30a or the first and second arms 30a and 30b are attached to the body 20 with one or more screws. In some embodiments, the first arm 30a or the first and second arms 30a and 30b are attached to the body with an adhesive. In some embodiments, the first arm 30a or the first and second arms 30a and 30b are made of a flexible material. In some embodiments the first arm 30a or the first and second arms 30a and 30b are made of a flexible material such as Acetal or Nylon plastic or other medical grade plastic. In some embodiments the Acetal or Nylon plastic or other medical grade plastic is reinforced with fiber glass reinforcement or other medical grade plastic. In some embodiments the reinforcement is present at 20, 21, 22, 23, 24, 25, 26, 27, 28, 29, 30, 31, 32, 33, 34, 35, 36, 37, 38, 39, or 40%, or any non-integer value within a range of 20% to 40%. In some embodiments the flexible material is Nylon, reinforced with 30% fiberglass. In some embodiments, the first arm 30a or the first and second arms 30a and 30b are shaped and positioned such that they allow concurrent opening of the endotracheal tube clamp 50 and the body 20, for example to ease the placement of the endotracheal tube. In some embodiments the first arm 30a or the first and second arms 30a and 30b are curved. In some embodiments, the first arm 30a or the first and second arms 30a and 30b are S shaped. In some embodiments, the device comprises a neck strap having ends seen at 112a, 112b and a neck strap connection 110a, 110b. In some embodiments, the neck strap connection 110a, 110b is attached to the first arm 30a or the first and second arms 30a and 30b. In some embodiments, the neck strap connection 110a is built into the first arm 30a. A number of neck strap configurations are consistent with the disclosure herein. In some embodiments, the neck strap connections are each a ring. In some embodiments the neck strap connections are each rectangular. In some embodiments, the neck strap connections are each a clip. In some embodiments, the neck strap connections are each a post. In some embodiments, the neck strap having ends seen at 112a, 112b fits around the patient's neck to further secure the device to the patient.

Figure 2A:
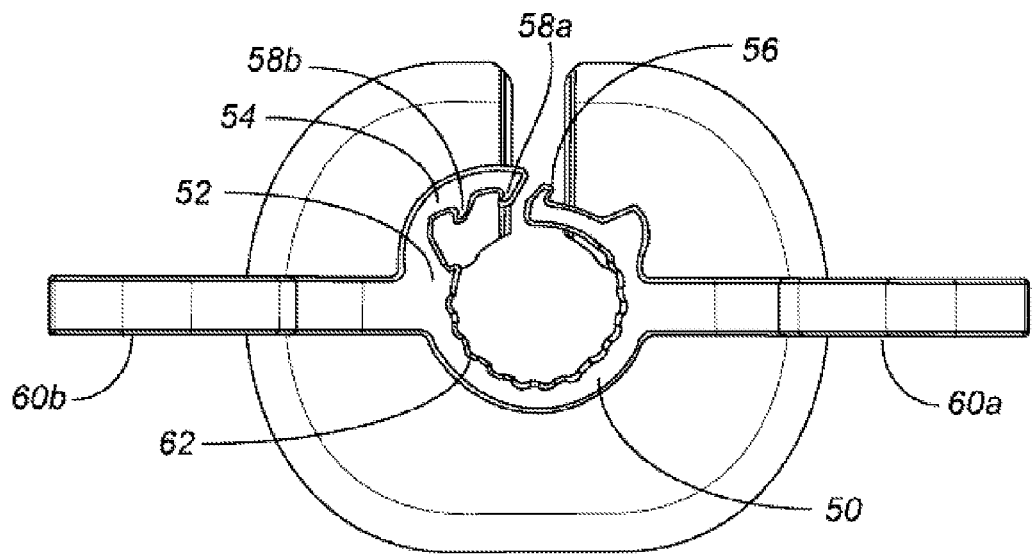
FIG. 2A shows an embodiment of the endotracheal tube clamp in the unlocked position.
Figure 2B:
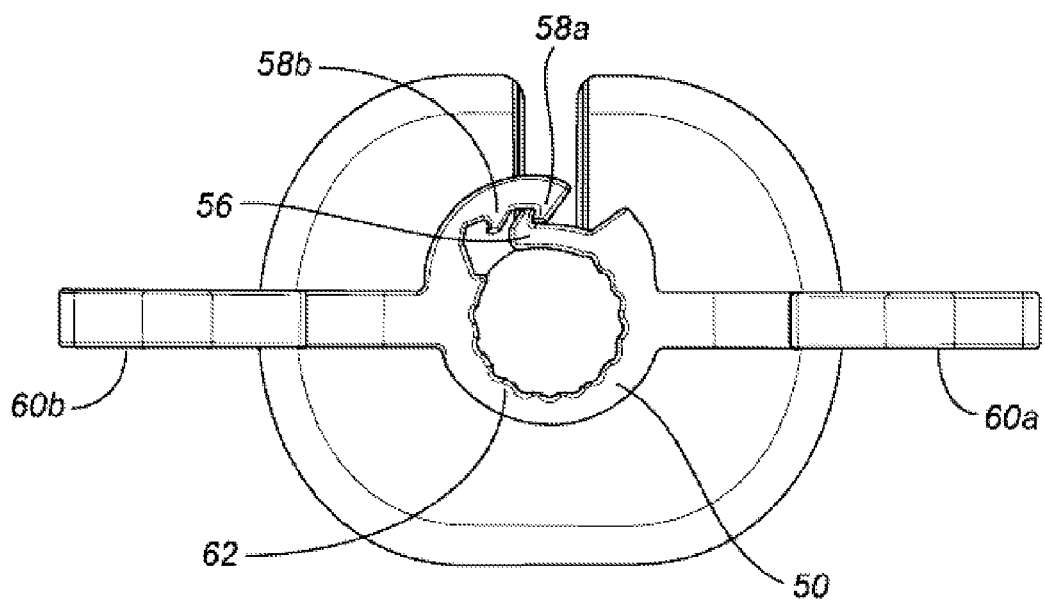
FIG. 2B shows an embodiment of the endotracheal tube clamp in the locked position.
Figure 2C:
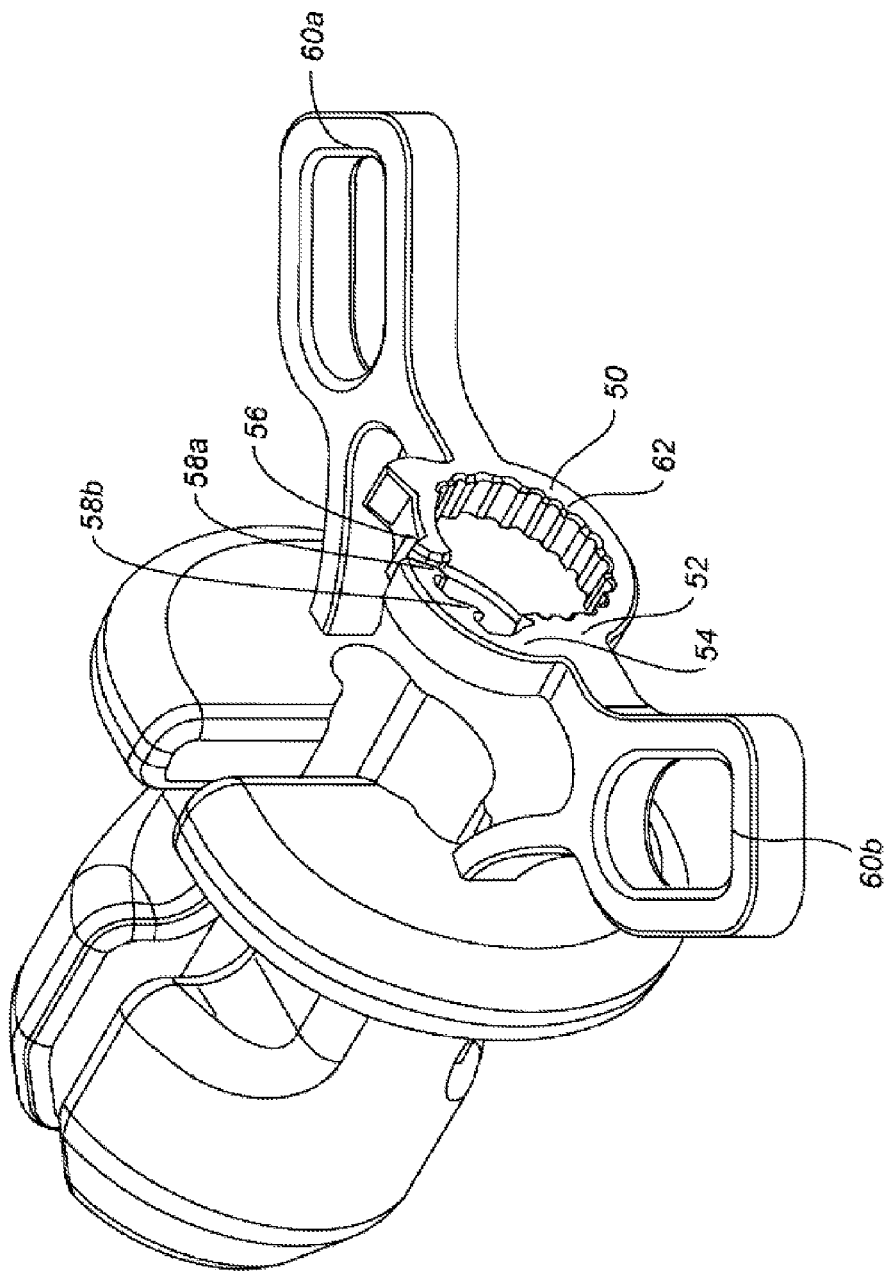
FIG. 2C presents an alternate view of the endotracheal tube clamp in the unlocked position as in FIG. 2A.

FIGS. 2A, 2B and 2C show alternate views and alternate configurations of an embodiment of the endotracheal tube clamp 50 joined to a body such as element 20 of FIG. 1, above. In some embodiments, the endotracheal tube clamp comprises a locking mechanism 52. In some embodiments, the endotracheal tube clamp 50 has multiple locking mechanisms 52. In some embodiments, the locking mechanism 52 has a single locking position. In some embodiments, the locking mechanism 52 has multiple locking positions. In some embodiments, the locking mechanism 52 comprises a latch system 54. In some embodiments, the latch system 54 comprises a hook 56 and a notch 58a that fit together. In some embodiments the latch system 54 comprises a hook 56 with a plurality of notches 58a, 58b. In some embodiments the latch system 54 comprises a plurality of hooks 56. In some embodiments each notch 58a-b defines a distinct locking position when interfaced with a hook 56. FIG. 2A shows a latch system 54 wherein a hook 56 is disengaged from notches 58a and 58b. FIG. 2B shows a latch system 54 wherein a hook 56 is engaged with a notch 58a in a first locked position. A second locked position for said latch system, not shown, is assumed wherein a hook 56 is engaged with a notch 58b. In some embodiments, the locking mechanism 52 comprises a handle 60a, or a pair of handles 60a and 60b for engaging and disengaging the locking mechanism 52. In some embodiments, the locking mechanism 52 comprises a pair of handles 60a, 60b for engaging and disengaging the locking mechanism 52. In some embodiments the handles 60a, 60b correspond to the neck strap connections 110a, 110b of FIG. 1, above. Alternate handle embodiments are presented in FIGS. 4A-C and 5A-B, and alternate handle embodiments not depicted therein are also contemplated. In some embodiments, the locking mechanism 52 comprises a nut and bolt. In some embodiments, the locking mechanism 52 comprises a magnet, a pair of magnets, or a larger plurality of magnets. In some embodiments, the locking mechanism 52 comprises a zip tie. In some embodiments, the locking mechanism 52 comprises a reversible zip tie. In some embodiments, an interior surface of the endotracheal tube clamp 50 comprises from one to a series of ridges 62. In some embodiments the series of ridges 62 can grip an enclosed device such as the endotracheal tube 100 of FIG. 3 when the endotracheal tube clamp 50 is in the locked position. In some embodiments, the endotracheal tube clamp 50 is made of a flexible material such as Acetal or Nylon plastic or other medical grade plastic. In some embodiments the Acetal or Nylon plastic or other medical grade plastic is reinforced with fiber glass reinforcement or other medical grade plastic. In some embodiments the reinforcement is present at 20, 21, 22, 23, 24, 25, 26, 27, 28, 29, 30, 31, 32, 33, 34, 35, 36, 37, 38, 39, or 40%, or any non-integer value within a range of 20% to 40%. In some embodiments the flexible material is Nylon, reinforced with 30% fiberglass. FIG. 2A shows an embodiment of an endotracheal tube clamp in an unlocked position. In some embodiments, the healthcare provider may lock the clamp by pushing one handle 60 towards the other, which causes the latch 54 to engage and the endotracheal tube clamp 50 to become locked. FIG. 2B shows an embodiment of an endotracheal tube clamp 50 in an unlocked position. In some embodiments, the endotracheal tube clamp 50 applies a compression force to the endotracheal tube 100 of FIG. 3 when the endotracheal tube clamp 50 is in the locked position. In some embodiments, a user such as a healthcare provider may unlock the clamp by applying a force to the handles 60a, 60b pushing one handle in the posterior direction and the other in the anterior direction causing the engaged latch 54 such as that of FIG. 2A to disengage, assuming the configuration of the disengaged latch 54 of FIG. 2B, and the endotracheal tube clamp 50 to release. In some embodiments, a user such as a healthcare provider may twist the handles 60 in opposite directions to release the endotracheal tube clamp 50. In some embodiments, the endotracheal tube clamp 50 may be unlocked by twisting either clockwise or counterclockwise.

Figure 3:
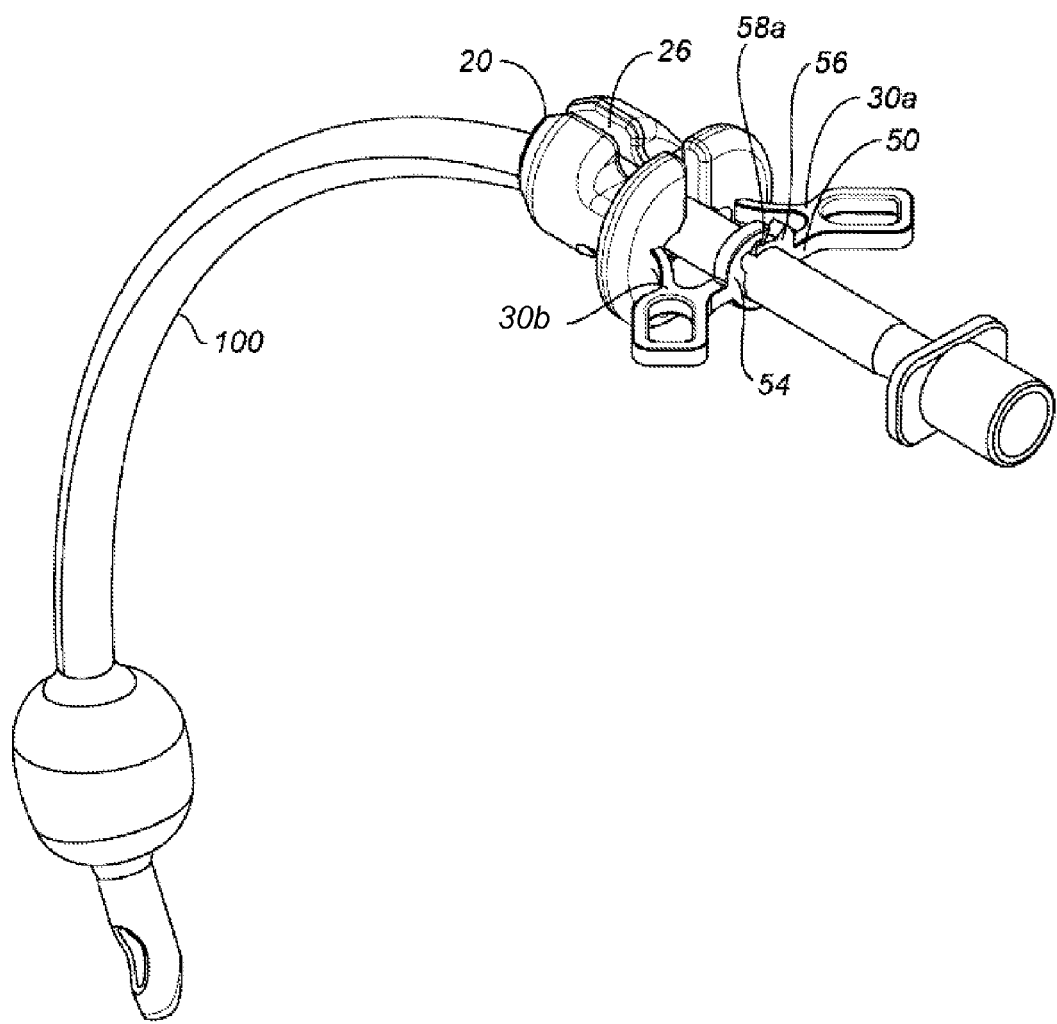
FIG. 3 shows the placement of an embodiment of the surgical bite block around an endotracheal tube.

FIG. 3 shows the placement of an embodiment of the bite block 10 around an endotracheal tube 100. In one method of placement of the bite block 10, after the patient is intubated, a user such as a healthcare provider may open the endotracheal tube clamp 50 by grasping the arms 30a, 30b and applying a bending moment, for example causing the latch 54 disengage as a result of the notch 58a or 58b to move laterally along the long axis of the device 10 relative to the hook 56, to open the endotracheal tube clamp 50 until the endotracheal tube 100 can pass through the locking mechanism 52. Alternately, a user such as a healthcare provider may open the endotracheal tube clamp 50 by grasping the arms 30a, 30b and applying a compressing motion to the arms 30a, 30b, for example causing the latch 54 to disengage as a result of the notch 58a or 58b passing over and along the hook 56 perpendicular to the long axis of the device 10. Other release methods are contemplated. By opening the endotracheal tube clamp, the slit 26 may also open to allow the endotracheal tube 100 to reach the first channel in the body 20. In some embodiments, the body 20 opens because the endotracheal tube clamp 50 is anchored into the lateral aspects of the body 20, and the first and second arms 30a, 30b transfer the bending deflection to the body 20. Once the endotracheal tube clamp 50 and the body 20 are placed around an endotracheal tube such as the endotracheal tube 100 the bite block may be allowed to translate along the longitudinal axis of the endotracheal tube 100 in the unlocked position. The user such as a healthcare provider may then slide the bite block 10 and introduce the body 20 into the patient's mouth in a position that provides the protection of the patient's teeth and soft tissues. Once the desired position is found, the user such as a healthcare provider may lock the clamp to secure the position of the bite block 10 relative to the endotracheal tube 100. A neck strap may then be attached, for example as seen in 112a, 112b of FIG. 1, to the neck strap connection 110a, 110b of FIG. 1 to further stabilize the construct by securing the surgical bite block around the patient's neck. In some embodiments, body dimensions such as round body dimensions allow for the surgical bite block to swivel around the mouth in a ball and socket fashion to adjust endotracheal tube position, for example to compensate for an endotracheal tube that may not be placed centered with respect to the mouth openings of the patient.

Figure 4A:
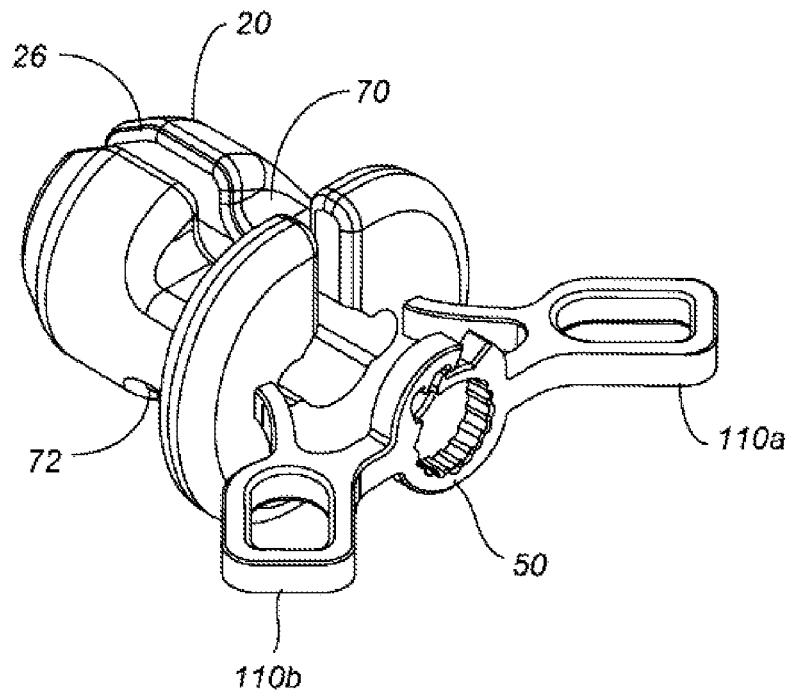
FIG. 4A shows an embodiment of the body without grooves for the patient's teeth and gums.
Figure 4B:
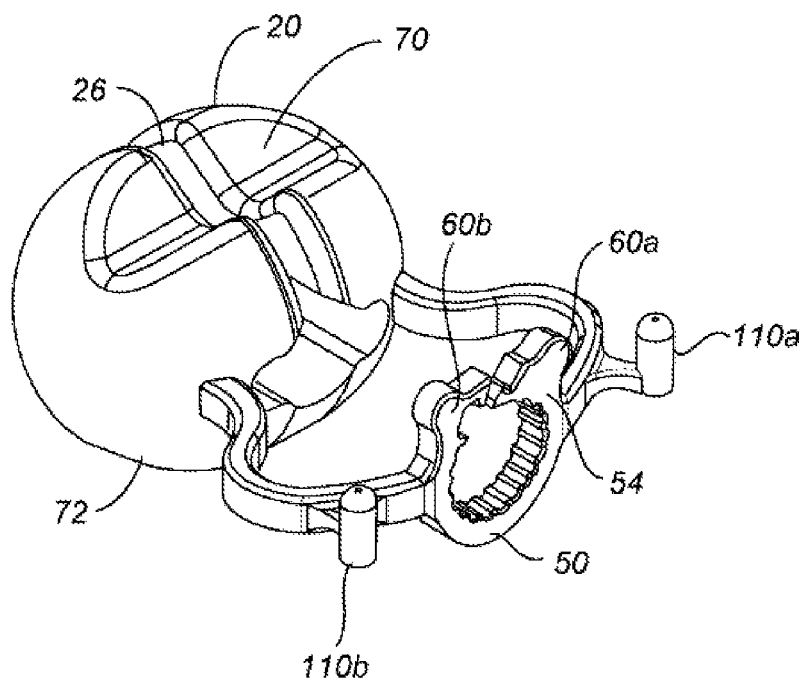
FIG. 4B shows an embodiment of the body with grooves for the patient's teeth and gums.
Figure 4C:
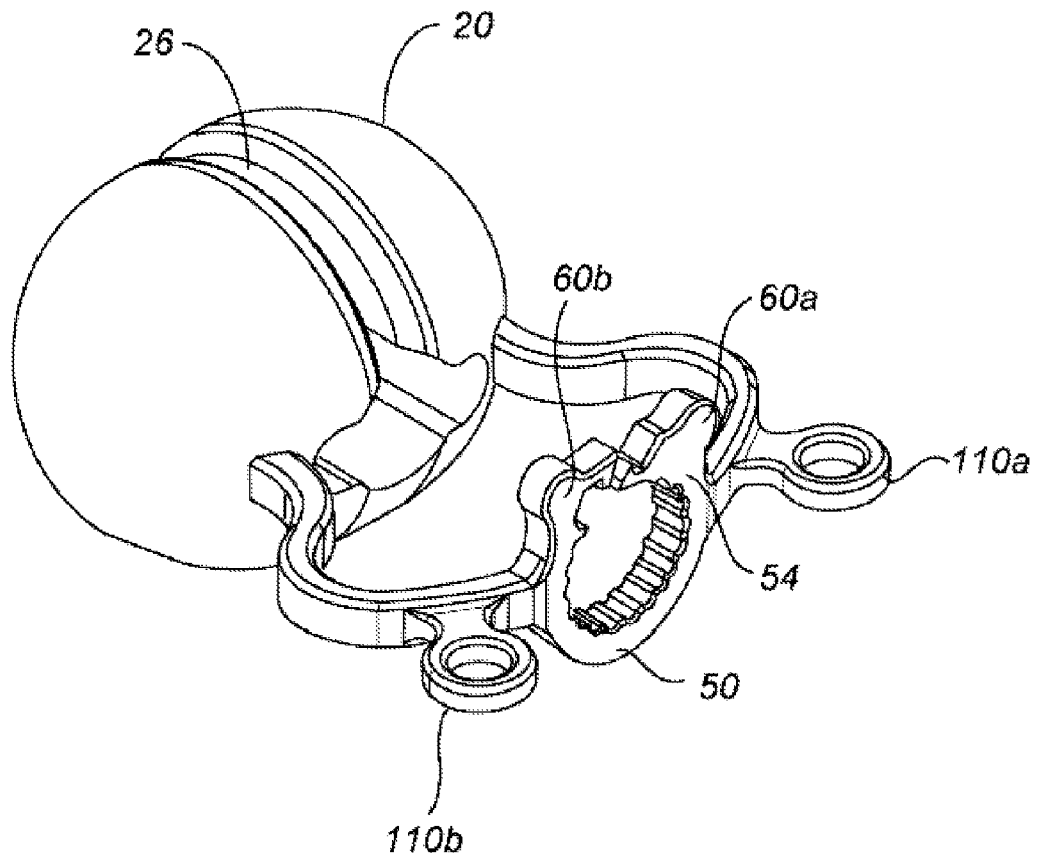
FIG. 4C shows an embodiment of the body with grooves for the patient's teeth and gums.

FIGS. 4A-C show embodiments of the bite block 10. In some embodiments the bite block 10 when properly deployed protects a patent's teeth, jaws or mouth from clenching damage. In some embodiments, such as those seen in FIGS. 4A-4B, the bite block 10 comprises a body with a first groove 70. In some embodiments, the patient's teeth or gums rest within the first groove 70, further securing the body 20 in the patient's mouth when the body 20 is properly deployed into a patient's mouth. In some embodiments, the body has a second groove 72. In some embodiments, the patient's lower teeth or gums rest in the second groove 72 and the patient's upper teeth and gums rest in the first groove 70 when the body 20 is properly deployed into a patient's mouth. In some embodiments, the first groove 70 extends circumferentially around the body 20. In some embodiments, either the first or second groove 70, 72 or both comprise a concave indent on the body 20. In some embodiments, the slit 26 intersects the first groove 70 or the second groove 72 or both the first groove and the second groove. In some embodiments, the slit 26 has an anti-pinch feature that protects the patient's lips. The anti-pinch feature may comprise a rounded edge or edges at regions likely to contact a patient's lips when the device is properly deployed. In some embodiments, the body 20 comprises a second set of concave indents to support the patient's lips. As seen in FIG. 4C, some embodiments lack one or more of the first groove 70 and the second groove 72

FIGS. 4A-C further shows embodiments of neck strap connections. A number of embodiments of neck strap connections are contemplated, as are embodiments lacking neck straps connections. Neck strap connections may be configured as rectangular or rounded rectangular structures, as in FIG. 4A elements 110a, 110b. Neck strap connections may be configured as a post or posts, as in FIG. 4B elements 110a, 110b, which can be inserted into a hole in a neck strap. Neck strap connections may be configured as circular or ring-like structures, as in FIG. 4C elements 110a, 110b, through which a neck strap may be threaded.

FIGS. 4A-C also vary in body structure. Any body structure may be combined with any neck strap connection, or no neck strap connection, in embodiments herein. In some embodiments the neck strap connection comprises a slit in each of the connecting arms 30a, 30b. In some embodiment the neck strap connection comprises a post 110a, 110b that can be inserted into a hole in the neck strap.

FIGS. 4B and 4C also depict alternate placements of handles 60a, 60b as nobs affixed to the latching mechanism to facilitate engagement and disengagement of the latch.

Figure 5A:
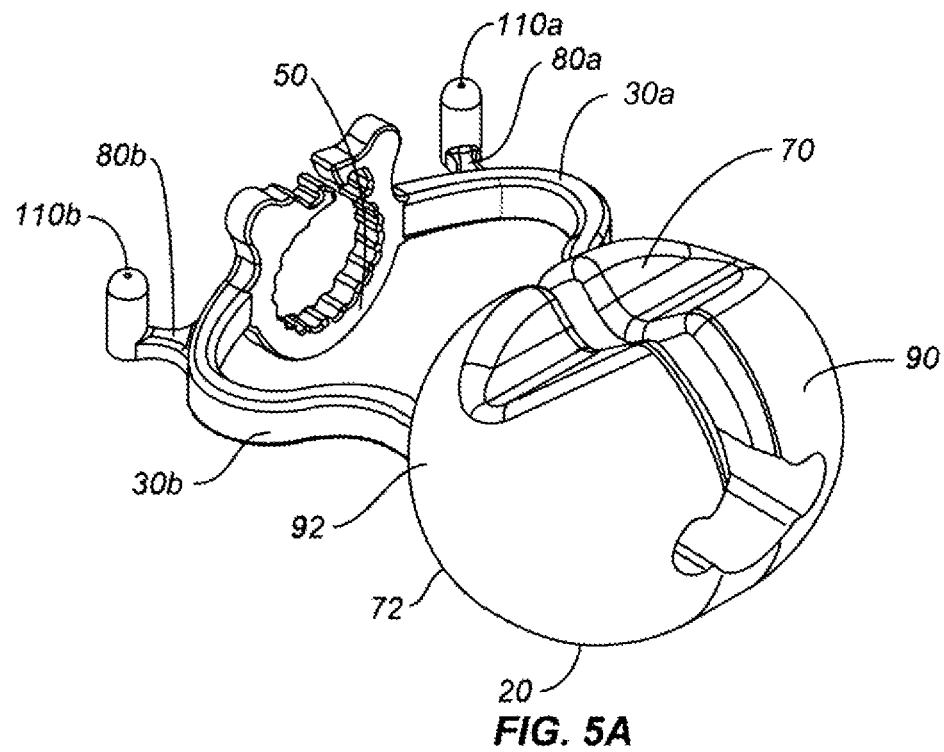
FIG. 5A shows an embodiment of the body with a bulbous shaped posterior aspect without grooves for the patient's teeth and gums.
Figure 5B:
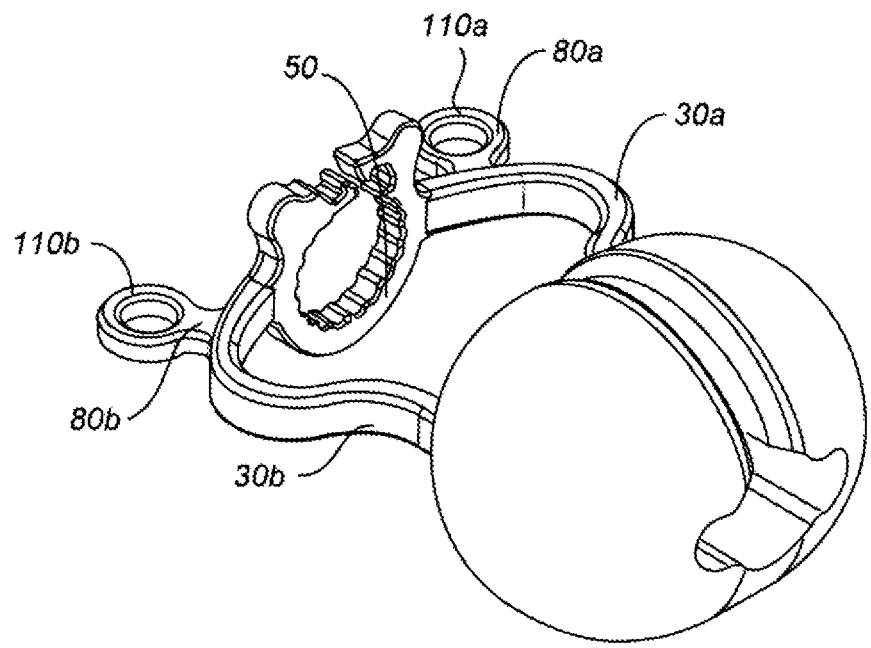
FIG. 5B shows an embodiment of the body with a bulbous shaped posterior aspect with grooves.

FIGS. 5A-B show embodiments of the body 20. In some embodiments, the body's 20 shape promotes the anchoring of the bite block 10 in the patient's mouth when the body is properly deployed. In some embodiments this may occur due to a natural tendency of the patient's mouth to rest in a semi-closed position. The patient's teeth or gums may then rest on the groove(s) thereby anchoring the construct in the patient's mouth. As seen in FIG. 5A, in some embodiments, the body 20 has an anterior aspect 92 and a posterior aspect 90. In some embodiments, the body's 20 posterior aspect 90 has a bulbous shape that passively anchors in the mouth by resting proximal to the front teeth or front gums. The body 20 may keep the patient's mouth open enough to clear the endotracheal tube 100 while minimizing stresses on both the patient's soft tissues and teeth. This embodiment may comprise a first groove 70 and a second groove 72 that provide space for the teeth or gums to rest on and further stabilizing the bite block 10 in the anterior-posterior axis, as depicted in FIG. 5A. As seen, for example, in FIG. 5B, some embodiments of the body 20 lack a first or a second groove. Accordingly, in some embodiments patient's teeth rest directly on the body or anterior to the body when the body is properly deployed in a patient's mouth.

In some embodiments, the bite block 10 may comprise finger supports, such as 80a, 80b seen in FIG. 5A, that allow the healthcare provider to open and close the endotracheal tube clamp. In some embodiments, the finger supports 80a, 80b are located between the first or second arm 30a, 30b and the endotracheal tube clamp 50. In some embodiments the finger supports 80a, 80b are a ring. In some embodiments the finger supports 80a, 80b are rectangular. In some embodiments, pushing the finger supports 80a, 80b towards each other locks the endotracheal tube clamp 50. In some embodiments, the neck strap connection, such as 110a, 110b comprises holes or slits located on the finger supports 80a, 80b. In some embodiments, the finger supports 80a, 80b are rectangular with an opening in the middle. In some embodiments, the neck strap connection such as 110a, 110b is the opening in the finger supports 80a, 80b. In some embodiments, the finger supports allow easy locking and unlocking of the endotracheal tube clamp 50.

Figure 6:
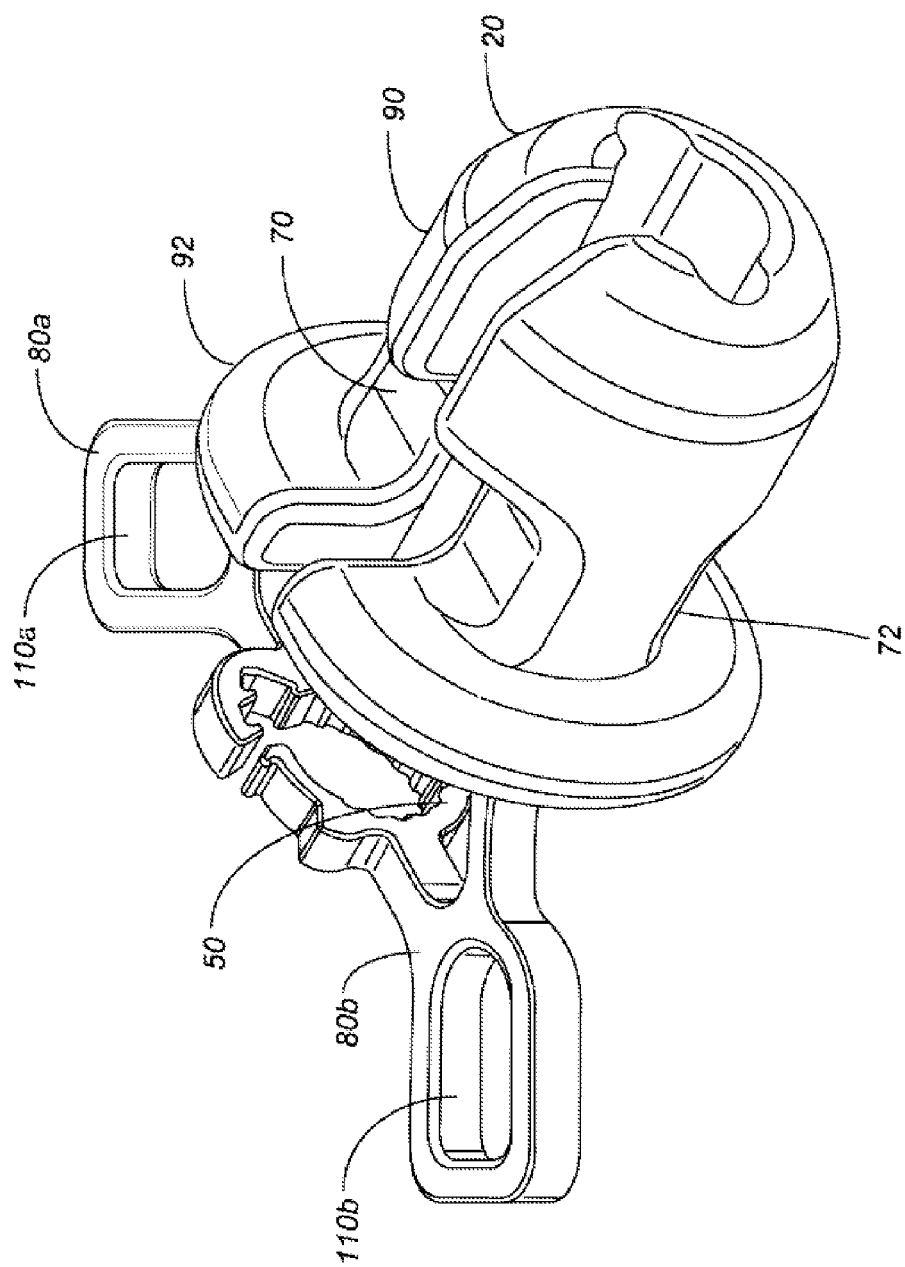
FIG. 6 shows an embodiment of the body with a bulbous shaped posterior aspect.

FIG. 6 shows an embodiment of the body 20 with a bulbous shaped posterior aspect 90. In some embodiments, the bulbous shaped posterior aspect 90 is combined with a cylindrical shaped anterior aspect 92. In some embodiments the anterior aspect is rectangular shaped or ovoid. In some embodiments the anterior aspect is bisected by a slit such as element 26 of FIG. 1.

Figure 7:
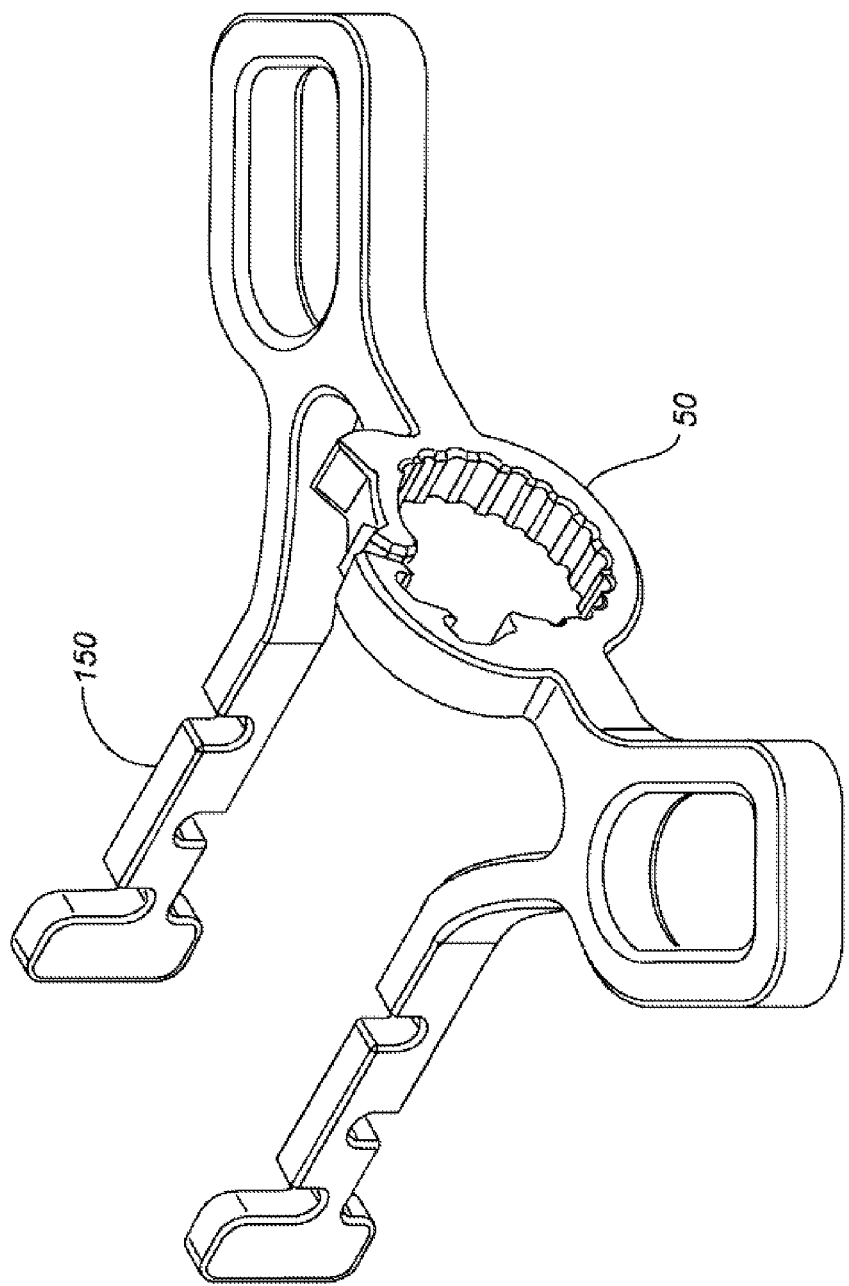
FIG. 7 shows an embodiment of a clamp lacking a body and having struts to which a body may be affixed.

FIG. 7 shows an isolated view of the endotracheal tube clamp 50 with features as indicated in the discussion of FIG. 1, above, showing struts 150 through which the clamp may be affixed to a body such as the body in FIG. 1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bite block comprising:
a body having an external side and a mouth side, said body comprising
  a) a silicone or medical grade foam portion sized and shaped to fit in a mouth of a person, wherein said portion comprises
    i) a first groove configured to fit top teeth of said person,
    ii) a second groove configured to fit bottom teeth of said person,
    iii) a posterior aspect that comprises a shape that is at least one of bulbous, cylindrical, and spherical, wherein the posterior aspect is configured to anchor the body in the mouth by being positioned proximal to the front teeth or gums, and wherein said posterior aspect of said body, when deployed into the mouth of said person, protects the mouth, teeth, or mouth and teeth of said person from clenching damage of said top teeth or said bottom teeth against said body;
  b) a first body channel running through the body from an external side of the body to a mouth side of the body through the posterior aspect, wherein the first body channel is sized to accommodate a first segment of an endotracheal tube therein,
  c) a second body channel extending peripherally from the first body channel, the second body channel having a smaller diameter than a diameter of the first body channel, the second body channel sized to accommodate a measuring device therein such as at least one temperature probe running through the body from the external side of the body to the mouth side of the body through the posterior aspect, and
  d) a slit extending from an outer surface of the body through the posterior aspect and at least one of the first groove and second groove and joining the first body channel, said slit comprising rounded edges at said outer surface configured to allow positioning of the body onto a previously intubated endotracheal tube; and
an endotracheal tube clamp coupled to the body, the endotracheal tube clamp comprising
  a) a first clamp channel substantially aligned with the first body channel and sized to accommodate a second segment of the endotracheal tube therein,
  b) a locking mechanism configurable in an open position and a closed position, said locking mechanism comprising a hook and a notch, wherein the hook and the notch, when the locking mechanism is in the closed position, cooperate to hold the endotracheal tube substantially in place relative to the first body channel and the first clamp channel by the hook engaging the notch, and c) at least one opening for threading a neck strap therethrough to substantially hold said bite block in place relative to the person when said portion is fit in the mouth of the person.

2. A bite block comprising:

a body having a silicone or medical grade foam portion sized and shaped to fit in a mouth of a person, wherein said body comprises a posterior aspect that passively anchors proximal to teeth of said person, wherein the posterior aspect comprises a shape that is at least one of bulbous, cylindrical, and spherical, and wherein said body, when deployed, protects the teeth of said person in contact with said body from clenching damage of said teeth against said body;

an endotracheal tube clamp coupled to the body or integral with the body, sized to accommodate an endotracheal tube therein;

a first channel running through the body from an external side to a mouth side of the body through the posterior aspect, the first channel sized to accommodate the endotracheal tube therein; a second channel extending peripherally from the first channel, the second channel having a smaller diameter than a diameter of the first channel, the second channel sized to accommodate a measuring device therein such as at least one temperature probe running through the body from the external side of the body to the mouth side of the body through the posterior aspect, and a slit extending from the first channel to an outer surface of the body through the posterior aspect, such that the bite block can be deployed onto an endotracheal tube after the endotracheal tube is intubated into the person.

3. The bite block of claim 2, comprising at least one opening for threading a neck strap therethrough to substantially hold said bite block in place relative to the person when said portion is fit in the mouth of the person.

4. The bite block of claim 2, wherein the slit comprises rounded edges at said outer surface.

5. The bite block of claim 2, wherein the body is substantially spherical, substantially cylindrical or substantially ovoid in shape.

6. The bite block of claim 2, wherein the endotracheal tube clamp comprises a locking mechanism.

7. The bite block of claim 6, wherein the locking mechanism has a single locking position.

8. The bite block of claim 6, wherein the locking mechanism has multiple locking positions.

9. The bite block of claim 8, wherein the locking mechanism comprises a latch.

10. The bite block of claim 8, wherein the locking mechanism comprises a pair of handles for opening and closing the locking mechanism.

11. The bite block of claim 2, wherein the body comprises a first groove for a patient's teeth or gums.

12. The bite block of claim 11, wherein the body comprises a second groove for the patient's teeth or gums opposite the first groove.

13. The bite block of claim 11, wherein the first groove extends around a circumference of the body.

14. The bite block of claim 2, wherein the body consists of medical grade foam.

15. The bite block of claim 2, where said body and said endotracheal tube clamp are removably connected.

* * * * *